US012622657B2

(12) United States Patent
Kroenke-Hille et al.

(10) Patent No.: US 12,622,657 B2
(45) Date of Patent: May 12, 2026

(54) ASSISTING SCAPULA POSITIONING IN CHEST X-RAY IMAGING

(71) Applicant: KONINKLIJKE PHILIPS N.V., Eindhoven (NL)

(72) Inventors: Sven Kroenke-Hille, Hamburg (DE); Daniel Bystrov, Hamburg (DE); Martin Bergtholdt, Hamburg (DE); Bernd Menser, Hauset (BE); Julien Thomas Senegas, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 184 days.

(21) Appl. No.: 18/710,634

(22) PCT Filed: Nov. 7, 2022

(86) PCT No.: PCT/EP2022/080931
§ 371 (c)(1),
(2) Date: May 16, 2024

(87) PCT Pub. No.: WO2023/088710
PCT Pub. Date: May 25, 2023

(65) Prior Publication Data
US 2025/0057491 A1 Feb. 20, 2025

(30) Foreign Application Priority Data
Nov. 16, 2021 (EP) ..................................... 21208474

(51) Int. Cl.
*A61B 6/00* (2024.01)
*A61B 6/04* (2006.01)
(Continued)

(52) U.S. Cl.
CPC .............. *A61B 6/0492* (2013.01); *A61B 6/46* (2013.01); *A61B 6/54* (2013.01); *G06T 7/0012* (2013.01);
(Continued)

(58) Field of Classification Search
CPC ........... A61B 5/70; A61B 6/04; A61B 6/0492; A61B 6/46; A61B 6/50; A61B 6/54
See application file for complete search history.

(56) References Cited

U.S. PATENT DOCUMENTS

| | | |
|---|---|---|
| 11,234,660 B2 | 2/2022 | Talgorn |
| 2012/0008739 A1 | 1/2012 | Hoernig |

(Continued)

FOREIGN PATENT DOCUMENTS

| | | |
|---|---|---|
| EP | 3498173 A1 | 6/2019 |
| EP | 3811866 A1 | 4/2021 |

(Continued)

OTHER PUBLICATIONS

PCT International Search Report, International application No. PCT/EP2022/080931, Feb. 6, 2023.
(Continued)

*Primary Examiner* — Dani Fox
(74) *Attorney, Agent, or Firm* — Larry Liberchuk

(57) ABSTRACT

The present invention relates to assisting scapula positioning in chest X-ray imaging. Provided is a system and related method for assisting subject positioning in chest X-ray imaging, wherein the system comprises an optical detection device (110), a user interface (130), and a processor (120), connected to the optical detection device (110) and the user interface (130). Thereby, the processor (120) is configured to receive an optical image signal of a rear view of the subject(S), determine a current positioning of a scapula of the subject(S) based on the optical image signal, wherein the
(Continued)

current positioning of the scapula is assessed as to whether and/or to which extent it would overlap or would not overlap a lung field of the subject to be imaged and determine a feedback for positioning the subject(S) and/or its scapula based on the determined current positioning of the scapula. The user interface (130) is configured to provide the feedback for positioning the subject.

15 Claims, 2 Drawing Sheets

(51) Int. Cl.
*A61B 6/46* (2024.01)
*G06T 7/00* (2017.01)

(52) U.S. Cl.
CPC ............... *G06T 2207/10012* (2013.01); *G06T 2207/10028* (2013.01); *G06T 2207/20081* (2013.01); *G06T 2207/20084* (2013.01)

(56) References Cited

U.S. PATENT DOCUMENTS

| | | | | |
|---|---|---|---|---|
| 2015/0228071 A1* | 8/2015 | Jockel | ................... | G06T 7/0012 |
| | | | | 382/132 |
| 2017/0224302 A1* | 8/2017 | Von Berg | ............... | A61B 6/466 |
| 2017/0322484 A1 | 11/2017 | Erhard | | |
| 2020/0330055 A1* | 10/2020 | Talgorn | .................. | A61B 6/461 |

FOREIGN PATENT DOCUMENTS

| | | |
|---|---|---|
| WO | WO2014033614 A1 | 3/2014 |
| WO | WO2016066444 A1 | 5/2016 |
| WO | WO2020138454 A1 | 7/2020 |

OTHER PUBLICATIONS

Joo Y-C. et al., "Comparison with Overlap Area of Scapular and Lung Field according to Position on Chest Radiography", Indian Journal of Science & Technology, vol. 9, No. 25, Jul. 18, 2016 (Jul. 18, 2016), XP055908063.

Delgarmi M. et al., "Automatic Landmark Detection of Human Back Surface from Depth Images via Deep Learning", World Journal of Clinical & Medical Images(WJCMI), vol. 1, Issue 1, pp. 30-42, 2022.

Namayega C. et al., "Contour Detection in Synthetic Bi-Planar X-Ray Images of the Scapula: Towards Improved 3D Reconstruction Using Deep Learning", 2020 IEEE 20th International Conference on BioInformatics and BioEngineering (BIBE), pp. 303-307, 2020.

Saito S. et al., "PIFuHD: Multi-Level Pixel-Aligned Implicit Function for High-Resolution 3D Human Digitization", IEEE Conference on Computer Vision and Pattern Recognition (CVPR), 2020, arXiv:2004.00452 [cs.CV].

Hatakeda H. et al., "Analysis of the Relationship Between the Scapular Posture and Surrounding Skin Mobility", Communication Society Technical Research Report, Japan, Institute of Electronics, Information and Communication Engineers (IEICE), vol. 1, No. 49, pp. 27-32, 2015.

* cited by examiner

ASSISTING SCAPULA POSITIONING IN CHEST X-RAY IMAGING

FIELD OF THE INVENTION

The present invention relates to medical imaging, and in particular to a computer-implemented method for assisting subject positioning in chest X-ray imaging, to a system for assisting subject positioning in chest X-ray imaging, and to a computer program element.

BACKGROUND OF THE INVENTION

In medical imaging, e.g. in X-ray imaging, appropriate subject positioning can be regarded as being crucial for achieving X-ray images of diagnostic quality.

In case of chest X-ray imaging, a scapula, i.e. shoulder-blade, must be rotated outside of the lung-field since otherwise relevant parts of the lung-field may be partially occluded, cover, which renders the image difficult to be read.

If the scapula positioning causes occlusion of or overlap with the lung field, it may be necessary to repeat the image acquisition, which is time-consuming, causes longer occupancy of the X-ray imaging device, and results in a higher radiation dose to the patient. Thereby, the required subject's pose is rather inconvenient and not easy to be taken, so that detailed instructions by the operator are required for achieving a proper scapula positioning. Further, time-pressure and a lack of experience, can result in an inappropriate subject positioning reducing the diagnostic quality of the x-ray image.

SUMMARY OF THE INVENTION

There may, therefore, be a need for improved means for at least assisting positioning of a subject in a manner allowing acquiring a medical image with a desired positioning of the scapula.

The object of the present invention is solved by the subject matter of the independent claims, wherein further embodiments are incorporated in the dependent claims.

According to a first aspect, there is provided a computer-implemented method for assisting subject positioning in chest X-ray imaging. The method comprises receiving an optical image signal of a rear view of the subject and determining a current positioning of a scapula of the subject based on the optical image signal, wherein the current positioning of the scapula is assessed as to whether and/or to which extent it would overlap or would not overlap a lung field of the subject to be imaged. Further, the method comprises determining a feedback for positioning the subject and/or its scapula based on the determined current positioning of the scapula and providing the feedback for positioning the subject.

In this way, the required subject's positioning and/or its scapula's positioning, which is rather inconvenient and not easy to be taken, can be assisted in an automatic manner by automatically determining and providing appropriate instructions to e.g. an operator, e.g. a radiographer, to achieve a good scapula positioning. Further, the above method is carried out radiation-free, since an optical image signal, e.g. from a camera or the like, is used, so that the radiation dose for the subject can be limited or even reduced.

In other words, in chest imaging it is desired the shoulder blade(s) to be rotated outside of the lung-field since otherwise relevant parts of a lung field may be masked and partially occluded, wherein the above method allows to evaluate and improve the positioning of the shoulder blade (s), i.e. the scapula (e), with respect of the positioning's impact on the imaging quality.

As used herein, a rear view of the subject or the optical image thereof may be understood as an image of the subject's back at the level of the chest and shoulder blades. Thereby, the optical image can be understood in distinction to an X-ray image as an image taken without radiation, wherein the optical image may be acquired by an optical detection device, such as an optical camera, a depth-resolving camera, or the like, with known relative position to the focal point of the focal point of an X-ray device, e.g. its X-ray tube, used for the actual X-ray imaging.

The depth information may be understood as e.g. pixel-wise information about a distance of the subject to the optical detection device and/or the X-ray device. It may also include a depth map. For example, elevations, depressions, flattenings, etc. of the subject can be recognized from this.

The feedback, which may be output graphically, e.g. via a display etc., via audio, e.g. via a loudspeaker, headphone, etc., or the like, may indicate that the positioning is already correct, at least in a sufficient manner. That is, the feedback may confirm correct positioning. However, if there is a deviation between the current positioning and a desired target positioning, the feedback may indicate how the positioning of the subject and/or scapula is to be changed to comply with the target or desired positioning, where it does not cover or overlap with a lung field of the subject to be imaged.

As used herein, the optical image signal may be indicative of an outward rotation of the scapula relative to a torso and/or a center of the subject's body. Thereby, with sufficient outward rotation, good visualization of the lung field can be accomplished.

In an embodiment, determining the current positioning of the scapula may comprise determining an arm and/or wrist positioning of the subject being indicative for the current scapula positioning from the optical image signal. For example, the exam which the subject undergoes may assume that the wrist lies on the hips and/or back of the subject. The above method allows this to be checked automatically from the measured optical image signal, e.g. camera signal, and the feedback and/or a warning can be communicated to the operator if required. Further, not in all cases, the subject is asked to position the wrist on the hips and/or back, as this is not always possible for the subject, for example, due to physical limitations. Therefore, it is also conceivable that the patient is asked to use a handhold mounted to e.g. the X-ray imaging device. e.g. detector. In this case, instead of detecting the wrist. e.g. the forearm of the subject may be detected and used to determine the scapula positioning.

According to an embodiment, a set of landmarks on or of the subject may be derived from the optical image signal to assess the current scapula positioning. For example, the set of landmarks, which are indicative for the positioning of the shoulder blade. i.e. the scapula, may be automatically detected in or from the optical image signal. e.g. via a deep convolutional neural network. If the landmarks are detected only on RGB channels of an optical detection device, their corresponding position in 3D space may be inferred from a depth channel, or alternatively, may be estimated using a stereo. i.e. multi-view, camera setup. Furthermore, it may also be possible to compute an estimated distance from a single RGB camera using a trained neural network. By way of example, given the detected set of landmarks, their constellation may be analyzed and compared to desired constellations for X-ray images of good quality regarding the scapula positioning. This can be accomplished by e.g. deriving a plane spanned by landmarks on the back, spanned by landmarks on the shoulder, the elbow and wrist on the left side as well as right side of the subject, and/or by calculating the angulation angles and comparing these angles to thresholds for achieving good scapula positioning, which may be obtained from clinical studies or the like. In this way, the scapula positioning can be determined radiation-free in a simple way and with high accuracy.

In an embodiment, a geometric relationship being indicative for the current scapula positioning may be determined from the set of landmarks. For example, the geometric relationship may be indicative of a desired constellation of good quality regarding the scapula positioning. By way of example, a constellation of the set of landmarks may be evaluated by grouping them to e.g. triangles, and calculating the angulation angles and comparing them against. e.g. previously learned, threshold angles for having the shoulder-blades fully rotated outside of the lung-field. In this way, the scapula positioning can be determined radiation-free in a simple way and with high accuracy.

According to an embodiment, a plane spanned by one or more extremities of the subject may be determined from the set of landmarks, and wherein the determined plane may be compared to a target value to derive the current scapula positioning therefrom. For example, the plane, or multiple planes, may be spanned by landmarks on the back, and/or may be spanned by landmarks on the shoulder, and/or may be spanned by the elbow and wrist of the subject. In this way, the scapula positioning can be determined radiation-free in a simple way and with high accuracy.

In an embodiment, wherein at least one angle between an arm of the subject and its torso and/or its body center and/or a detector of an X-ray imaging device used for the chest X-ray imaging is determined from the set of landmarks, and wherein the at least one determined angle is compared to a target value to derive the current scapula positioning therefrom. For example, the angulation angle may be calculated and compared to a threshold for achieving good scapula positioning, which may be obtained from clinical studies or the like. In this way, the scapula positioning can be determined radiation-free in a simple way and with high accuracy.

According to an embodiment, the plane and/or angle may be determined for both sides of the subject, i.e. for both scapulae, and a symmetry and/or congruence of both sides is determined to derive the current scapula positioning therefrom. In this way, the scapula positioning can be determined radiation-free in a simple way and with high accuracy.

In an embodiment, one or more contours of the subject and/or one or more surface properties of the subject may be derived from at least the optical image signal to assess the current scapula positioning. For example, alternatively or additionally to detecting and/or determining landmarks, other features being predictive for the scapulae positioning can be automatically detected and assessed. These features may involve contours, e.g. parts of the outline, or surface properties of the subject, e.g. curvature. In this way, the scapula positioning can be determined radiation-free in a simple way and with high accuracy.

According to an embodiment, the feedback may comprise or form a trigger signal configured to control and/or prevent image acquisition based on the scapula positioning. For example, the method may be implemented in or may be connected to an acquisition system of the X-ray imaging device in such a way that a warning is communicated to the operator if the subject has moved its scapulae just before the acquisition, e.g. after the operator has left the acquisition room, or the like. Further, the method may allow to disable the acquisition release button if such a potential quality issue has been detected. In this way, X-ray image acquisition can be controlled based on the scapula positioning.

In an embodiment, the optical image signal may be received by a classifier and/or model trained on annotated training data, and wherein the classifier determines the current scapula positioning based on at least the optical image signal. For example, the optical image signal may be captured and provided by an optical detection device, which may be an RGB camera, an RGB-D camera, i.e. a depth-resolving camera, a stereo camera setup, or the like. The classifier and/or model may be configured to map the optical image signal to a prediction of the scapula overlap, which may be trained on sufficient, e.g. annotated, optical image signal-target positioning data or pairs. In this way, several camera setups can be used to provide the optical image signal.

According to an embodiment, a depth information data may be received from a depth channel of an optical detection device used to capture the optical image signal of the rear view of the subject. For example, the depth information may be received from a depth-resolving camera with known relative position to the focal point of the x-ray tube, wherein the camera may be mounted on e.g. the tube head or the like.

In an embodiment, a depth information data may be received directly from a 3D depth map based on at least the optical image signal. For example, instead of using a 2-step approach of first detecting features, such as landmarks, contours, or the like, and then assessing them, also a single forward model trained in an end-to-end manner may be used.

According to an embodiment, a depth information data may be determined based on a stereo optical detection device used to capture the optical image signal of the rear view of the subject.

According to an embodiment, the depth information data may be received from a classifier trained on annotated training data, and wherein the classifier determines the current scapula positioning based on at least the optical image signal. For example, features derived from or detected in the optical image signal and/or depth information data may be fed into the classifier, e.g. a neural network, trained on annotated data. Further, the classifier may also be configured and/or trained to take further factors into account, such as BMI, subject thickness or the proportions of the subject's extremities. In this way, the scapula positioning can be determined radiation-free in a simple way and with high accuracy.

According to a second aspect, there is provided a system for assisting subject positioning in chest X-ray imaging. The system may be configured to carry out the method according to the first aspect. The system comprises an optical detection device, a user interface, and a processor connected to the optical detection device and the user interface. Thereby, the processor is configured to receive an optical image signal of a rear view of the subject, determine a current positioning of a scapula of the subject based on the optical image signal, wherein the current positioning of the scapula is assessed as to whether and/or to which extent it would overlap or would not overlap a lung field of the subject to be imaged, and to determine a feedback for positioning the subject and/or its scapula based on the determined current positioning of the scapula. Further, the user interface is configured to provide the feedback for positioning the subject.

In this way, the required subject's positioning and/or its scapula's positioning, which is rather inconvenient and not easy to be taken, can be assisted in an automatic manner by automatically determining and providing appropriate instructions to e.g. an operator, e.g. a radiographer, to achieve a good scapula positioning.

For example, the optical detection device may be mounted with known relative position to a focal point of an X-ray imaging device used for the X-ray imaging. By way of example, the optical detection device may be a single camera, e.g. a RGB camera or the like, a depth-resolving camera, e.g. a RGB camera with a depth channel, a time-of-flight optical detection device, a stereo camera setup, etc.

The processor may utilize a classifier or model to determine, e.g. predict, the scapula positioning from the optical image signal. Optionally, the classifier or model may be configured to further consider a depth information data, which may be provided by a depth channel of the optical detection device, by the stereo camera setup, or the like.

In an embodiment, the system may be integrated or connected to an X-ray imaging device to disable e.g. an acquisition release button if the scapula positioning does not meet or match a target positioning.

According to a third aspect, there is provided a computer program element, which when executed by a processor is configured to carry out the method of the first aspect, and/or to control a system according to the second aspect.

According to a fourth aspect, there is provided a computer-readable storage or transmission medium, which has stored or which carries the computer program element according to the third aspect.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
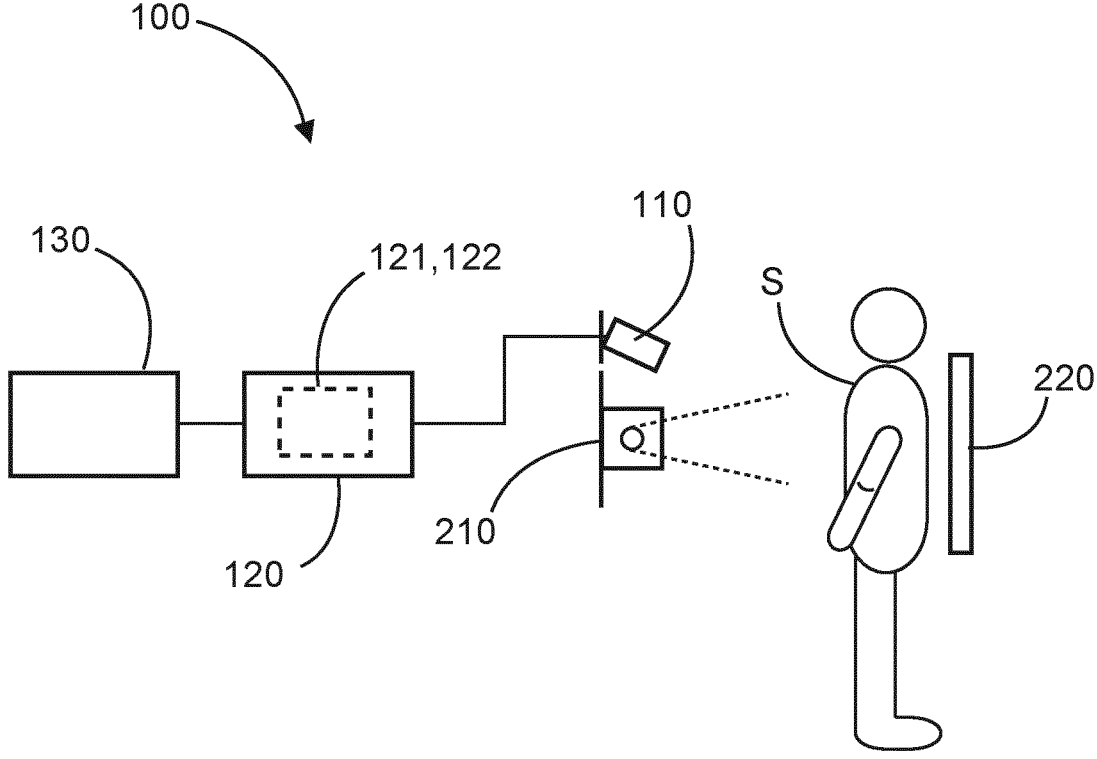
FIG. 1 shows in schematic block diagram a system for assisting subject positioning in chest X-ray imaging, according to an embodiment.

FIG. 1 shows in schematic block diagram a system 100 that is configured to assist positioning of a subject S in chest X-ray imaging, wherein the X-ray imaging may utilize an X-Ray device with a radiation source 210, e.g. an X-ray tube, and a detector 220. The system 100 comprises an optical detection device 110, a processor 120, and a user interface 130.

The optical detection device 110 is arranged to capture a rear view of the subject S in an optical image signal. It can be implemented in different forms, for example as a single RGB camera, a depth-resolving camera, a RGB-D camera, a time-of-flight optical detection device, a stereo camera setup, or the like. The optical detection device 110 may be arranged with known relative position to the focal point of the x-ray tube, e.g. mounted on the radiation source 210.

The processor 120 is connected to the optical detection device 110 and to the user interface 130. The processor 120 is configured to access a memory 121 storing a computer program element suitable to process the optical image signal received from the optical detection device 110. Further, the processor 120 may be configured to access a classifier and/or model 122 that is configured, e.g. trained based on optical image signal-scapula positioning-pairs, to map a prediction of a scapula-lung field overlap to the optical image signal received from the optical detection device. Further, the processor 120 is configured to receive the optical image signal from the optical detection device 110 and determine a current positioning of a scapula of the subject S based on the optical image signal, wherein the current positioning of the scapula is assessed as to whether and/or to which extent it would overlap or would not overlap a lung field of the subject to be imaged. Further, the processor 120 is configured to determine a feedback for positioning the subject S and/or its scapula based on the determined current positioning of the scapula. The feedback may comprise a graphical feedback, an audio feedback, or the like, suitable to provide an operator or medical stuff with information whether the positioning of the subject is already correct, or whether and/or how the positioning is to be changed to comply with a desired target positioning.

Figures 2A, 2B:
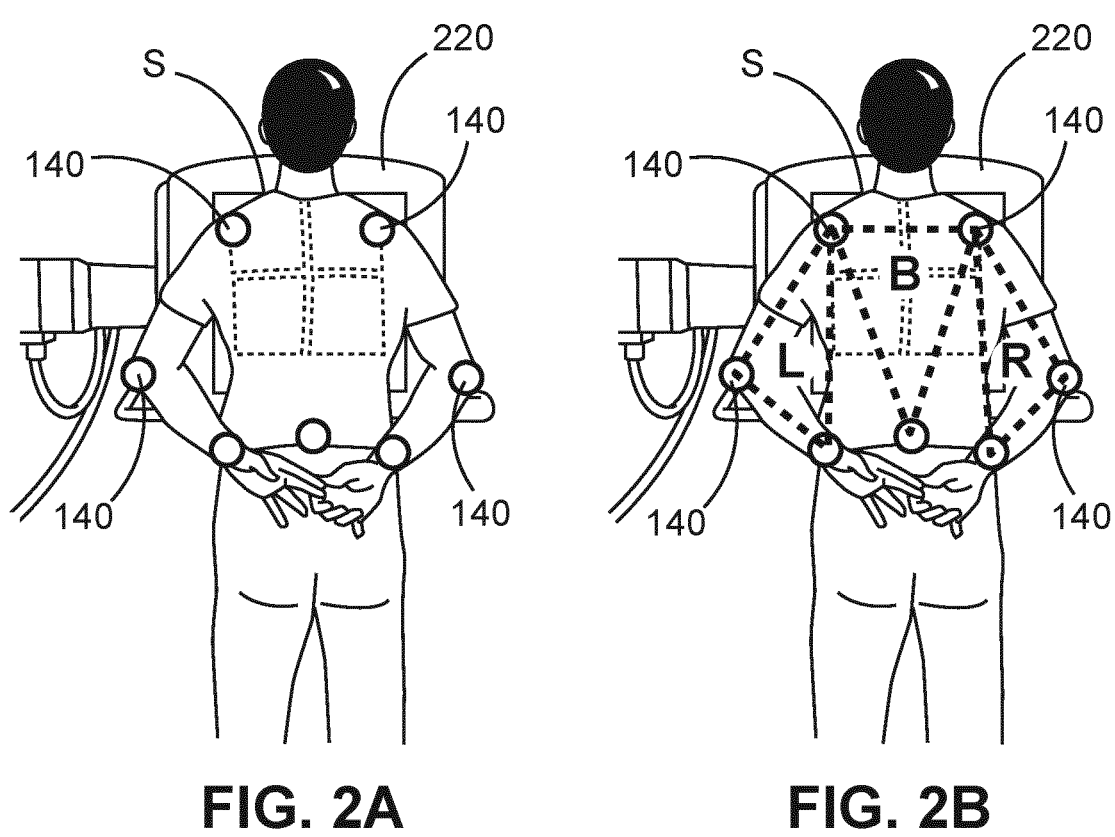
FIG. 2A shows schematically a determination of a scapula positioning, according to an embodiment.
FIG. 2B shows schematically a determination of a scapula positioning, according to an embodiment.

FIG. 2A shows schematically a determination of a scapula positioning, wherein a set of landmarks 140 on or of the subject S is derived from the optical image signal to determine and/or assess the current scapula positioning. The set of landmarks 140 may be determined by the processor 120, e.g. by utilizing one or more imaging analyzing techniques and/or the classifier and/or model 122 from the optical image signal received from the optical detection device 110. For example, the set of landmarks 140 may comprise one or more landmarks being indicative for or formed by body characteristics of the subject S, wherein FIG. 2A exemplary shows landmarks 140 located at the should, arm and/or elbow, wrist, forearm, or other suitable body parts of the subject S.

FIG. 2B shows schematically that the processor 120 may be configured to determine a geometric relationship being indicative for the current scapula positioning from the set of landmarks 140. For example, a plane spanned by one or more extremities of the subject may be determined from the set of landmarks, wherein the determined plane may be compared to a target value to derive the current scapula positioning therefrom. For example, the plane, or multiple planes, may be spanned by landmarks on the back, and/or may be spanned by landmarks on the shoulder, and/or may be spanned by the elbow and wrist of the subject. By way of example, the constellation of the landmarks 140 is evaluated by grouping them to triangles B (back). L (left side) and R (right side), calculating the angulation angles of L with B and R with B and comparing them against threshold angles for having the shoulder-blades fully rotated outside of the lung-field.

Figure 3:
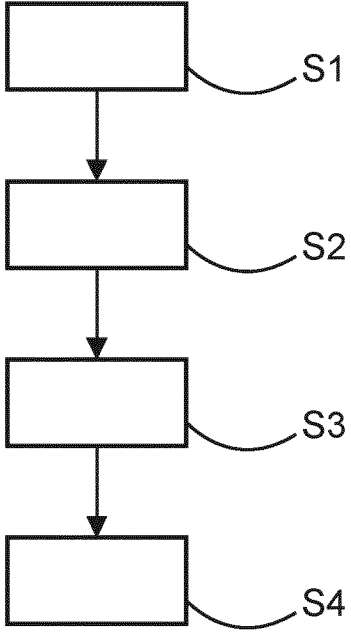
FIG. 3 shows in a flowchart a method for assisting subject positioning in chest X-ray imaging, according to an embodiment.

FIG. 3 shows in a schematic flow chart a computer-implemented method for assisting subject positioning in chest X-ray imaging. The method may be carried out by the system 100 as described above.

In a step S1, an optical image signal of a rear view of the subject S is received. For example, the optical image signal, which may comprise one or more images, image frames, etc., may be captured and provided by the optical detection device 110.

In a step S2, a current positioning of a scapula of the subject S based on the optical image signal, wherein the current positioning of the scapula is assessed as to whether and/or to which extent it would overlap or would not overlap a lung field of the subject to be imaged. For example, the current positioning may be determined by the processor 120 as described above.

In a step S3, a feedback for positioning the subject S and/or its scapula based on the determined current positioning of the scapula. For example, the feedback may be determined by the processor 120 as described above.

In a step S4, the feedback for positioning the subject S may be provided via the user interface 130 as described above.

Optionally, determining the current positioning of the scapula comprises determining an arm and/or wrist positioning of the subject S being indicative for the current scapula positioning from the optical image signal.

Optionally, a set of landmarks 140 on or of the subject S is derived from the optical image signal to assess the current scapula positioning.

Optionally, a geometric relationship being indicative for the current scapula positioning is determined from the set of landmarks 140.

Optionally, a plane spanned by one or more extremities of the subject S is determined from the set of landmarks 140, and wherein the determined plane is compared to a target value to derive the current scapula positioning therefrom.

Optionally, at least one angle between an arm of the subject S and its torso and/or its body center and/or a detector plane of an X-ray imaging device is determined from the set of landmarks, and wherein the at least one determined angle is compared to a target value to derive the current scapula positioning therefrom.

Optionally, the set of landmarks 140 is determined on both sides of the subject S, i.e. for both scapulae, and a symmetry and/or congruence of both sides is determined to assess the current scapula positioning.

Optionally, one or more contours of the subject and/or one or more surface properties of the subject S are derived from at least the optical image signal to assess the current scapula positioning.

Optionally, the optical image signal data is received by a classifier trained on annotated training data, and wherein the classifier determines the current scapula positioning based on at least the optical image signal Optionally, a depth information data is received from a depth channel of the optical detection 110.

Optionally, a depth information data is received directly from a 3D depth map based on at least the optical image signal.

Optionally, a depth information data is determined based on a stereo optical detection device used to capture the optical image signal of the rear view of the subject S.

Optionally, the feedback comprises or forms a trigger signal configured to control and/or prevent image acquisition based on the scapula positioning. For example, the system 100 may be connected to the radiation source 210 and/or detector 220 in order to control image acquisition based on the determined positioning and/or feedback.

In another exemplary embodiment, a computer program or computer program element is provided that is characterized by being configured to execute the method steps of the method according to one of the preceding embodiments, on the system 100.

The computer program element might therefore be stored to be executed by the processor 120, which might also be part of an embodiment. This processor unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

The computer program element may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 system
110 optical detection device
120 processor
121 memory
122 classifier and/or model
130 user interface
140 set of landmarks
210 radiation source
220 detector

The invention claimed is:

1. A computer-implemented method for assisting subject positioning in chest X-ray imaging, comprising:
   receiving an optical image signal of a rear view of the subject;
   determining a current positioning of a scapula of the subject based on the optical image signal, wherein the current positioning of the scapula is assessed as to whether and/or to which extent it would overlap or would not overlap a lung field of the subject to be imaged;
   determining a feedback for positioning the subject and/or its scapula based on the determined current positioning of the scapula; and
   providing the feedback for positioning the subject.

2. The method of claim 1, wherein determining the current positioning of the scapula comprises determining an arm and/or wrist positioning of the subject being indicative for the current scapula positioning from the optical image signal.

3. The method of claim 1, wherein a set of landmarks on or of the subject is derived from the optical image signal to assess the current scapula positioning.

4. The method of claim 3, wherein a geometric relationship being indicative for the current scapula positioning is determined from the set of landmarks.

5. The method of claim 3, wherein a plane spanned by one or more extremities of the subject is determined from the set of landmarks, and wherein the determined plane is compared to a target value to derive the current scapula positioning therefrom.

6. The method of claim 3, wherein at least one angle between an arm of the subject and its torso and/or its body center and/or a detector plane of an X-ray imaging device is determined from the set of landmarks, and wherein the at least one determined angle is compared to a target value to derive the current scapula positioning therefrom.

7. The method of claim 3, wherein the set of landmarks is determined on both sides of the subject for both scapulae, and a symmetry and/or congruence of both sides is determined to assess the current scapula positioning.

8. The method of claim 1, wherein one or more contours of the subject and/or one or more surface properties of the subject are derived from at least the optical image signal to assess the current scapula positioning.

9. The method of claim 1, wherein the optical image signal is received from a classifier or a model trained on annotated training data, and wherein the classifier or the model determines the current scapula positioning based on at least the optical image signal.

10. The method of claim 1, wherein a depth information data is received from a depth channel of an optical detection device used to capture the optical image signal of the rear view of the subject.

11. The method of claim 1, wherein a depth information data is received directly from a 3D depth map based on at least the optical image signal.

12. The method of claim 1, wherein a depth information data is determined based on a stereo optical detection device used to capture the optical image signal of the rear view of the subject.

13. The method of claim 1, wherein the feedback comprises or forms a trigger signal configured to control and/or prevent image acquisition based on the scapula positioning.

14. A system for assisting subject positioning in chest X-ray imaging, comprising:
   an optical detector;
   a user interface; and
   a processor, connected to the optical detector and the user interface, wherein the processor is configured to:
      receive an optical image signal of a rear view of the subject;
      determine a current positioning of a scapula of the subject based on the optical image signal, wherein the current positioning of the scapula is assessed as to whether and/or to which extent it would overlap or would not overlap a lung field of the subject to be imaged; and
      determine a feedback for positioning the subject and/or its scapula based on the determined current positioning of the scapula;
   wherein the user interface is configured to provide the feedback for positioning the subject.

15. A non-transitory computer-readable medium for storing executable instructions, which cause a method for assisting subject positioning in chest X-ray imaging to be performed, the method comprising:
   receiving an optical image signal of a rear view of the subject;
   determining a current positioning of a scapula of the subject based on the optical image signal, wherein the current positioning of the scapula is assessed as to whether and/or to which extent it would overlap or would not overlap a lung field of the subject to be imaged;
   determining a feedback for positioning the subject and/or its scapula based on the determined current positioning of the scapula; and
   providing the feedback for positioning the subject.

* * * * *